(12) United States Patent
Anderson et al.

(10) Patent No.: US 6,521,797 B1
(45) Date of Patent: Feb. 18, 2003

(54) OXIME CARBOXYLIC ACID DERIVATIVE PRECURSORS

(75) Inventors: Denise Anderson, Zürich (CH); Georg Frater, Winterthur (CH)

(73) Assignee: Givaudan AG, Dubendorf (CH)

( * ) Notice: Subject to any disclaimer, the term of this patent is extended or adjusted under 35 U.S.C. 154(b) by 0 days.

(21) Appl. No.: 09/376,776

(22) Filed: Aug. 17, 1999

(30) Foreign Application Priority Data

Aug. 17, 1998 (EP) .............................................. 98115403

(51) Int. Cl.$^7$ .............................................. C07C 47/21
(52) U.S. Cl. ..................................................... 568/448
(58) Field of Search ......................................... 568/448

(56) References Cited

U.S. PATENT DOCUMENTS

| | | |
|---|---|---|
| 3,624,091 A | 11/1971 | Uerdingen et al. |
| 4,014,915 A | 3/1977 | Itoh |
| 4,416,686 A | 11/1983 | Martin |

FOREIGN PATENT DOCUMENTS

| | | |
|---|---|---|
| DE | 1 809 385 | 6/1970 |
| DE | 2 227 921 | 6/1973 |
| DE | 28 37 204 | 3/1980 |
| DE | 32 24787 A1 | 1/1984 |
| GB | 1 048 346 | 11/1966 |
| JP | 62-286961 | 9/1986 |
| WO | WO 95/04809 | 2/1995 |

OTHER PUBLICATIONS

Patent Abstract of Japan, publication No. JP 8151356 (1996)(Derwent Publication No. XP–002124668).
Patent Abstract of Japan, publication No. JP 7173140 (1995) (Derwent Publication No. XP–002124669).
Kabara, J.J., *Cosmet. Sci. Technol. Ser.*, (16)181–208, (1997).
Menendez, E., et al., *Synthesis*, 72–74, (1993).
Itoh, M., et al., *Tetrahedron Letters*, (49) 4393–4394, (1975).

*Primary Examiner*—T. A. Solola
(74) *Attorney, Agent, or Firm*—Andrew N. Parfomak; Norris, McLaughlin & Marcus, P.A.

(57) ABSTRACT

The present invention is an oxime carboxylic acid derivative having the formula I:

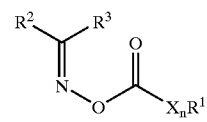

wherein n is 1 or 0, X is O, $R^2$ and $R^3$ being part of an oxime $R^2R^3C\!\!=\!\!NOH$ are individually, substituted or unsubstituted, branched or unbranched alkyl-, alkenyl-, akinyl-, cycloalkyl-, cycloalkenyl-, or aromatic radical and contain less than 30 carbon atoms, and $R^1$ is a substituted or unsubstituted, branched or unbranched alkyl-, alkenyl-, akinyl-, cycloalkyl-, cycloalkenyl-, alkoxyalkyl-, aryloxyaryl-, alkoxyaryl-, aryloxyalkyl-, or aromatic radical, or $X_nR^1$ is

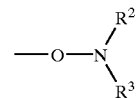

which are useful as precursors for the delivery of organoleptic compounds, especially for flavors, fragrances and masking agents, and/or antimicrobial compounds.

1 Claim, No Drawings

OXIME CARBOXYLIC ACID DERIVATIVE PRECURSORS

FIELD OF THE INVENTION

The present invention relates to oxime carboxylic acid derivatives and the use of oxime carboxylic acid derivatives as precursors for (a) organoleptic compounds, especially for flavors, fragrances, (b) masking agents, and/or (c) antimicrobial compounds.

BACKGROUND OF THE INVENTION

A principal strategy currently employed to impart odors to consumer products is the admixing of a fragrance, flavor, masking agent or antimicrobial compound directly into the product to be treated. There are, however, several drawbacks to this strategy. The fragrance material may, for example, be too volatile and/or too soluble, resulting in, e.g., fragrance loss during manufacturing, storage, and use. Many fragrance materials are also unstable over time. This again results in fragrance loss during storage.

In many consumer products, it is desirable for the fragrance to be released slowly over time. Microencapsulation and inclusion complexes, especially with cyclodextrins, have been used to help decrease volatility, improve stability, and provide slow-release properties. However, these methods are, for a number of reasons, often not successful. In addition, cyclodextrins are too expensive to use commercially.

Fragrance precursors used to impart scent into fabrics during a washing cycle in the presence of a lipase-containing detergent are reportedly described in WO 95/04809. The fragrance precursors contained in the detergent and/or in the softener are cleaved by the lipase yielding a single odoriferous compound; either an odoriferous alcohol, aldehyde, or ketone. In this way, a prolonged scenting effect on the fabric is obtained.

SUMMARY OF THE INVENTION

An object of the present invention is to provide new precursors for organoleptic and/or antimicrobial compounds with varying activities.

Another object of the invention is to provide new precursors that are stable under conventional transport and storage conditions.

Another object of the invention is to provide precursors that supply different active compounds simultaneously or successively.

One embodiment of the present invention is an oxime carboxylic acid derivative precursor of the formula I:

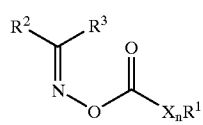

I wherein n is 1 or 0, X is O or N, $R^2$ and $R^3$ are part of an oxime $R^2R^3C=NOH$ and $R^1$ is a substituted or unsubstituted, branched or unbranched alkyl-, alkenyl-, alkynyl, cycloalkyl-, cycloalkenyl-, alkoxyalkyl-, aryloxyaryl-, alkoxyaryl-, aryloxyalkyl-, or aromatic radical, or $X_nR^1$ represents

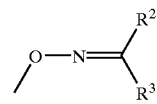

and upon decomposition the precursor forms an organoleptic compound, a masking agent, and/or an antimicrobial compound.

Another embodiment of the invention is a composition that includes a compound selected from the following group: formula I, formula II, formula III, and mixtures thereof.

Another embodiment of the invention is a process for prolonging the effect of diffusion of a characteristic odor of an odoriferous compound on human skin that includes applying a composition containing at least one compound selected from the group consisting of formula I, formula II, formula III, and mixtures thereof to a surface of the skin.

Another embodiment is a process for prolonging the effect of diffusion of a characteristic odor of an odoriferous compound in laundry products, detergents or fabric softeners that includes applying a composition containing at least one compound selected from the group consisting of formula I, formula II, formula III, and mixtures thereof into a laundry product, a detergent or a fabric softener.

Another embodiment is a method for dosing a composition with a fragrance that includes adding a fragrance precursor selected from the group consisting of formula I, formula II, formula III and mixtures thereof to a composition selected from the group consisting of a cosmetic, a laundry product, a detergent, a fabric softener, a beverage, a food, an animal feed, a tobacco product, an air freshener, a candle, and a cleaning composition.

Another embodiment is a carboxylic acid derivative having the formula I

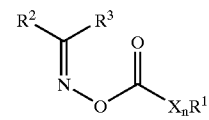

I wherein n is 1 or 0, X is O or N, $R^2$ and $R^3$ are an oxime $R^2R^3C=NOH$ and $R^1$ is a substituted or unsubstituted, branched or unbranched alkyl-, alkenyl-, alkynyl, cycloalkyl-, cycloalkenyl-, alkoxyalkyl-, aryloxyaryl-, alkoxyaryl-, aryloxyalkyl- or aromatic radical, or $X_nR^1$ represents

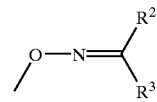

DETAILED DESCRIPTION OF THE INVENTION

In the present invention, certain oxime carboxylic acid derivatives have been found to be useful as organoleptic precursors. These oxime carboxylic acid derivatives are defined by formula I below:

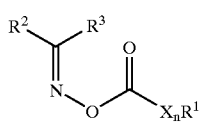

I wherein n is 1 or 0, X is O or N, $R^2$ and $R^3$ are part of an oxime $R^2R^3C=NOH$, and $R^1$ is a substituted or unsubstituted, branched or unbranched alkyl-, alkenyl-, alkynyl, cycloalkyl-, cycloalkenyl-, alkoxyalkyl-, aryloxyaryl-, alkoxyaryl-, aryloxyalkyl- or aromatic radical, preferably with 1 to 30 C atoms, or $X_nR^1$ is

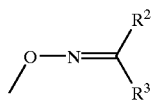

The compounds of formula I are not limited to any particular stereoisomer. Thus, the present invention includes all possible stereoisomers including E/Z isomers, enantiomers, diastereomers, as well as mixtures thereof.

In the present invention, $R^1$ may be selected from the following groups: oxo, hydroxo, carboxylic acid, ester, carbonate, carbamate, amide, amine, aryl, cycloalkyl, cycloalkenyl, oxime carboxylic acid derivative, and nitrile. Thus, for example $R^1$ may be substituted by at least one ester and/or carbonate group, that forms at least an alcohol, phenol, aldehyde, and/or ketone after cleavage of the oxime carboxylic acid derivative. $R^1$ may also be substituted with at least one carbamate and/or nitrile that forms an amine and/or a nitrile after cleavage of the oxime carboxylic acid derivative.

If X=N and n=1, $R^1$ may also represent the radical of an amino acid $NH_2R^1$ or its derivatives.

In an oxime carboxylic acid derivative according to the present invention, when X is O and n is 1, $R^1$ is the radical of an alcohol or phenol or the enol form of an aldehyde or ketone, all represented by the general formula $R^1OH$.

In another embodiment of the oxime carboxylic acid derivative of the present invention, when X is N and n is 1, —$NR^1$ represents the radical R'R"N— of an amine R'R"NH and R' and R" are independently, branched or unbranched, substituted or unsubstituted alkyl-, alkenyl-, alkinyl-, cycloalkyl-, cycloalkenyl- or aromatic radicals or either R' or R" may be hydrogen.

In another embodiment of the oxime carboxylic acid derivative of the present invention, when n is 0 and R' is substituted with a hydroxy group, the oxime carboxylic acid derivative after cleavage forms a lactone. At least one of the yielded decomposition products, i.e. the oxime, alcohol, phenol, aldehyde, amine, lactone and/or nitrile is organoleptic, especially odoriferous, has masking activity, and/or antimicrobial activity.

The present invention includes as compounds of specific oxime carboxylic acid derivatives represented by the formula II:

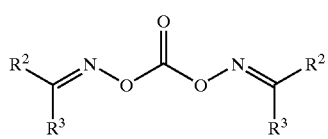

II and oxime carboxylic acid derivatives of formula III:

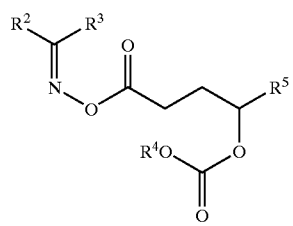

III wherein $R^2$ and $R^3$ are defined as set forth in formula I, $R^5$ is branched or unbranched, substituted or unsubstituted alkyl-, alkenyl-, alkynyl, cycloalkyl-, cycloalkenyl- or aromatic radical $R^4$ is $R^1$. For example, $R^4$ may be the radical of an alcohol, phenol, or the enol form of an aldehyde or ketone. In the present invention, precursors of fragrant alcohols, phenols, aldehydes or ketones are preferred.

In the present invention, a "precursor" is a compound that after decomposition under activating conditions, forms one of the following odoriferous oximes: 1,5-dimethyl-bicyclo [3.2.1]octan-8-one oxime; 2,4,4,7-tetramethyl nona-6, 8-dien-3-one oxime; 5-methyl-heptan-3-one oxime; or 1-bicyclo [2.2.1]hept-5-en-2-yl-ethanone oxime.

The present invention also includes non-organoleptic oxime precursors so long as they are effective as odor masking and/or antimicrobial agents and/or if other cleavage products thereof have at least one of the features set forth above.

The compounds of formula I may be odorless or nearly odorless at room temperature, atmospheric conditions and about 20% to 100% relative humidity. Under activating conditions, however, the compounds of formula I are cleaved and one or more active compounds with organoleptic and/or antimicrobial properties are generated. Such active compounds include oximes and optionally ketones, aldehydes, alcohols, phenols, lactones, amines, and/or nitriles.

In the present invention, the terms "activate," "activating," or "activating conditions" are used interchangeably. These terms are intended to mean conditions that lead to cleavage of the precursors and thereby to the liberation of the desired active compound(s), i.e., compounds with organoleptic, odor masking, and/or antimicrobial action. Such activating conditions may be obtained using, for example, skin bacteria, especially axilla bacteria, an enzyme such as a protease or a lipase, elevated temperature, acidic or alkaline pH-values, or a combination of at least two of these activating conditions.

As set forth above, compound of formula I, upon cleavage, forms at least one oxime and optionally one or more aldehydes, ketones, alcohols, phenols, lactones, amines, and/or nitriles. At least one of these cleavage products has organoleptic, antimicrobial, and/or odor masking activities. Accordingly, a compound of formula I permits the development of useful consumer products with enhanced organoleptic, antimicrobial, and/or masking properties.

The ketone, aldehyde, lactone, alcohol, phenol, amine, and nitrile cleavage products are preferably organoleptic and are useful as, e.g., fragrances, masking agents, and/or antimicrobial agents. Accordingly, compounds of formula I may be used as precursors in organoleptic compositions, e.g. fragrances, as precursors for masking agents, and/or as precursors for antimicrobial agents.

The oxime carboxylic acid derivatives of formula I may act as fragrance, odor masking, and/or antimicrobial precursors in, for example, personal care products; laundry products; cleaning compositions, such as all-purpose and hard surface cleaners; pet care products; and environment scents, such as air fresheners and candles.

The fragrance and odor masking agent precursors of the invention may be used individually in an amount effective to enhance or to mask the characteristic odor of a material. More commonly, however, these compounds are mixed with other fragrance or odor masking components in an amount sufficient to provide the desired odor characteristics. An "effective amount" in this respect means an amount of about 0.01 to about 15% by weight, specifically an amount of 0.1 to 10% by weight and more specifically an amount of 0.2 to 2% by weight, which amount, of course, is strongly dependent as well on the specific precursor compound used as on its specific usage. The examples set forth below provide representative "effective" amounts of the present compounds that are sufficient to provide the desired odor characteristics. Moreover, a person skilled in the art will have knowledge of how to make best use of the precursors of the invention.

In the present invention, because the active compounds are generated in situ the desired effect is prolonged and the substantivity on different substrates, especially on fabrics, is enhanced. For example, if two or more active compounds are provided, they may be generated, depending on the specific precursor and/or the activating conditions, simultaneously or successively. Further, the precursors of the invention provide slow release of the active compounds.

Examples of organoleptic ketones that may be generated by the cleavage of the compounds of formula I include:
2-heptyl-cyclopentanone; 2,2,6,10-tetramethyltricyclo-[5.4.0.0(6,10)]-undecan-4-one; benzylacetone*; carvone*; 1,2,3,5,6,7-hexahydro-1,1,2,3,3,-pentamentyl-4H-inden-4-one*; methyl heptenone*; dimethyl octenone*; 2-(butan-2-yl)-cyclohexanone*; 2-hexyl-cyclopent-2-en-1-one*; 2-(1-methylethyl)-5-methyl-cyclohexanone*; 2-(2-methylethyl)-5-methyl-cyclohexanone*; 3-methyl-cyclopentadecanone; 4-tert-pentyl-cyclohexanone*; 3-oxo-2-pentyl-cyclopentane-acetic acid methyl ester**; 1-(1,2,3,4,5,6,7,8-octahydro-2,3,8,8-tetramethyl-2-naphthalenyl)-ethanone*; 3-methyl-5-propyl-cyclohex-2-en-1-one*, wherein one asterisk (*) indicates the preferred ketones and two asterisk (**) indicate the more preferred ketones.

Examples of organoleptic aldehydes that may be generated by the cleavage of the compounds of formula I include:
2,6,10-trimethylundec-9-enal*; 1,2,3,4,5,6,7,8-octahydro-8,8-dimethyl-2-napthalenecarboxaldehyde; tridecanal; 2-[4-(1-methylethyl)phenyl]-ethanal; 4-carboxaldehyde-1,3,5-trimethyl-cyclohex-1-ene*; 1-carboxaldehyde-2,4-dimethyl-cyclohex-3-ene*; 1 carboxaldehyde-4-(4-hydroxy-4-methylpentyl)-cyclohex-3-ene*; heptanal*; 2,6-dimethyl-hept-5-enal; decanal**; dec-9-enal; dec-4-enal; 2-methyldecanal*; undec-10-enal**; undecanal*; dodecanal; 2-methyl-undecanal; octanal**; nonanal*; 3,5,5-trimethylhexanal; undec-9-enal**; 2-phenylpropanal*; 4-methyl-phenyl acet-aldehyde*; 3,7-dimethyl-octanal*; dihydrofarnesal**; 7-hydroxy-3,7-dimethyl-octanal*; 2,6-dimethyl-oct-5-enal; 2-(4-(1-methylethyl)phenyl)-ethanal*; 3-(3-isopropyl-phenyl)-butanal**; 2-(3,7-dimethyoct-6-en-oxy)-ethanal; 1-carboxaldehyde-4-(4-methyl-3-penten-1-yl)-cyclohex-3-ene*; 2,3,5,5,-tetramethyl-hexanal; longifolic aldehyde; 2-methyl-4-(2,6,6-trimethylcyclohex-2-en-1-yl)-butanal*; 2-methyl-3-(4-tert-butylphenyl)propanal**; 4-(1,1-dimethyl-ethyl)-benzenepropanal*; 2-[4-(1-methyl-ethyl)phenyl]-propanal; alpha-methyl-1,3-benzodioxole-5-propanal*; 3,7-dimethyl-oct-6-enal*; 2-methyl-3-(p-isopropylphenyl)-propionaldehyde*; 4-(4-hydroxy-4-methyl-pentyl)-cyclohex-3-en-1-carboxaldehyde**; alpha-methyl-1,3-benzodioxole-5-propanal*; 1-carboxaldehyde-4-(1,1-dimethylethyl)-cyclo-hexane; 4-(octahydro-4,7-methano-5H-inden-5-ylidene)-butanal; [(3,7-dimethyl-6-octenyl)oxy]-acetaldehyde**, wherein one asterisk (*) indicates the preferred aldehydes and two asterisk (**) the more preferred aldehydes.

Examples of organoleptic alcohols and phenols that may be generated by the cleavage of the compounds of formula I include:
amyl alcohol; hexyl alcohol*; 2-hexyl alcohol*; heptyl alcohol*; octyl alcohol*; nonyl alcohol*; decyl alcohol*; undecyl alcohol*, lauryl alcohol*, myristic alcohol; 3-methyl-but-2-en-1-ol*; 3-methyl-1-pentanol; cis-3-hexenol*; cis4-hexenol*; 3,5,5-trimethyl hexanol; 3,4,5,6,6-pentamethylheptan-2-ol*; citronellol*; geraniol*; oct-1-en-3-ol; 2,5,7-trimethyl octan-3-ol; 2-cis-3,7-dimethyl-2,6-octadien-1-ol; 6-ethyl-3-methyl-5-octen-1-ol*; 3,7-dimethyl-octa-3,6-dienol*; 3,7-dinethyloctanol*; 7-methoxy-3,7-dimethyl-octan-2-ol*; cis-6-nonenol*; 5-ethyl-2-nonanol; 6,8-dimethyl-2-nonanol*; 2,2,8-trimethyl-7(8)-nonen-3-ol; nona-2,6-dien-1-ol; 4-methyl-3-decen-5-ol*; dec-9-en-1-ol; benzylalcohol; 2-methyl undecanol; 10-undecen-1-ol; 1-phenyl ethanol*; 2-phenyl ethanol*; 2-methyl-3-phenyl-3-propenol; 2-phenyl propanol*; 3-phenyl propanol*; 4-phenyl-2-butanol; 2-methyl-5-phenyl pentanol*; 2-methyl-4-phenyl-pentanol*; 3-methyl-5-phenyl-pentanol*; 2-(2-methylphenyl)-ethanol*; 4-(1-methylethyl)benzene methanol; 4-(4-hydroxyphenyl)-butan-2-one*; 2-phenoxy ethanol*; 4-(1-methylethyl)-2-hydroxy-1-methyl benzene; 2-methoxy-4-methyl phenol; 4-methyl phenol; anisic alcohol*; p-tolyl alcohol*; cinnamic alcohol*; vanillin*; ethyl vanillin*; eugenol*; isoeugenol*; thymol; anethol*; decahydro 2-naphthalenol; borneol*; cedrenol*; farnesol*; fenchyl alcohol*; menthol*; 3,7,11-trimethyl-2,6,10-dodecatrien-1-ol; alpha ionol*; tetrahydro ionol*; 2-(1,1-dimethylethyl)-cyclohexanol*; 3-(1,1-dimethylethyl)-cyclohexanol*; 4-(1,1-dimethylethyl) cyclohexanol*; 4-isopropyl cyclohexanol; 6,6-dimethyl-bicyclo [3.3.1]hept-2-ene-2-ethanol; 6,6-dimethyl-bicyclo[3.1.1]hept-2-ene-methanol*; p-menth-8-en-3-ol*; 3,3,5-trimethyl cyclohexanol; 2,4,6-trimethyl-3-cyclohexenyl-methanol*; 4-(1-methylethyl)-cyclohexyl-methanol*; 4-(1,1-dimethylethyl)cyclohexanol; 2-(1,1-dimethylethyl)-cyclohexanol; 2,2,6-trimethyl-alpha-propyl cyclohexane propanol*; 5-(2,2,3-trimethyl-3-cyclo-pentenyl)-3-methylpentan-2-ol*; 3-methyl-5-(2,2,3-trimethylcyclopent-3-en-1-yl)pent-4-en-2-ol*; 2-ethyl-4-(2,2,3-trimethyl-cyclopent-3-en-1-yl)but-2-en-1-ol*; 4-(5,5,6-trimethyl-bicyclo[2.2.1]hept-2-yl)-cyclohexanol*; 2-(2-methylpropyl)-4-hydroxy-4-methyl-tetrahydropyran*; 2-cyclohexyl propanol*; 2-(1,1-dimethylethyl)-4-methyl cyclohexanol*; 1-(2-tert-butyl-cyclohexyloxy)-2-butanol*; 1-(4-isoporpyl-cyclohexyl)-ethanol*; 1-(4-hydroxyphenyl)-butan-3-one; 2,6- dimethyl-oct-7-en-2-ol*; 2,6-dimethyl-heptan-2-ol*; 3,7-dimethyl-octa-1,6-dien-3-ol*, wherein one asterisk (*) indicates the preferred alcohols and two asterisk (**) indicate the more preferred alcohols.

Examples of polyalcohols that may be generated by the cleavage of the compounds of formula I include for example: diols such as, diethylene glycol, propylene glycol, triethylene glycol, 4,4'-dicyclohexyldiol, N,N'-bis-(2-hydroxyethyl)-ethylenediamine, 1,3-bis-(4-hydroxybutyl)-1,1,3,3-tetramethyl-disiloxane, 1,4-bis-(hydroxymethyl)-cyclohexane, N-butyldiethanolamine; triols such as, glycerol, 1,3,5-cyclohexanetriol, triethanolamine; sugars such as, furanoside and pyranoside sugars such as glucose, fructose; and polymers such as, hydroxyethylcellulose and hydroxypropyl-cellulose.

Examples of lactones that may be generated by the cleavage of the compounds of formula I include:
6-methyl-pyran-2-one; 5-heptydihydro-2(3H)-furanone*; 5-pentyldihydro-2(3H)-furanone*; 5-(3-hexenyl)dihydro-5-methyl-(Z)-2(3H)-furanone; 5-hexyldihydro-5-methyl-2(3H)-furanone; 5-hexyldihydro-2(3H)-furanone*; 5-octyldihydro-2(3H)-furanone; 8-(1-methylethyl)-1-oxaspiro[4.5]-decan-2-one*; 8-methyl-1-oxaspiro[4.5]-decan-2-one; 8-ethyl-1-oxaspiro[4.5]-decan-2-one; 5-(1,5-dimethyl-4-hexenyl)-dihydro-2(3H)-furanone; 2-oxo-5-butyl-tetrahydrofuran*; 4-methyl-5-pentyl-dihydro-2(3H)-furan-2-one; 5-hexyldihydro-5-methyl-2(3H)-furanone; dihydro-5-methyl-5-vinyl-2(3H)-furanone; octahydro-2H-1-benzopyran-2-one; tetrahydro-6-pentyl-2H-pyran-2-one; tetrahydro-6-hexyl-2H-pyran-2-one; tetrahydro-6-heptyl-2H-pyran-2-one; tetrahydro-6-(3-pentenyl)-(E)-2H-pyran-2-one; tetrahydro-6-(2-pentenyl)-(Z)-2H-pyran-2-one, wherein one asterisk (*) indicates the preferred lactones.

Examples of organoleptic amines that may be generated by the cleavage of the compounds of formula I include:
anthranilic acid 1-methyl-1-(4-methyl-cyclohex-3-enyl) ethyl ester; benzopyrrole, 8,8-di(1H-indol-3-yl)-2,6-dimethyl-octane-2-ol; anthranilic acid allyl ester; anthranilic acid 1,5-dimethyl-1-vinyl-4-hexenyl ester; 2-aminobenzoic acid methyl ester*; methyl anthranilic acid N-(2-methylpent-1-en-1-yl) ester; anthranilic acid phenylethyl ester*; 2-methylamino-benzoic acid methyl ester*; 6-methyltetrahydro-quinoline; isobutyl N-methyl anthranilate; (Z)-3-hexenyl 2-aminobenzoate*, wherein one asterisk (*) indicates the preferred organoleptic amines.

In the present invention, a wide variety of non-organoleptic amines may also be generated upon cleavage of a precursor compound. For example, a list of suitable primary and secondary cosmetic amines which may be generated upon cleavage of a precursor compound of the present invention may be found in, e.g., *Cosmetic Ingredient Handbook;* edited by Joanne M. Nikitakis, which reference is incorporated by reference as if recited in full herein. Examples of surfactant amines that may be generated upon cleavage of a precursor compound of the present invention may be found in, e.g., *Surfactants Europa,* edited by Gordon L. Hollis, which reference is also incorporated by reference as if recited in full herein.

Precursor compounds of the present invention may also be used to generate amino acids. Such amino acids include, for example, glycine, leucine, tyrosine, serine, glutamic acid, aspartic acid, phenylalanine, alanine, lysine, arginine, histidine, cysteine, valine, proline, tryptophan, isoleucine, methionine, asparagine, glutamine, and threonine.

In the present invention, when cleaved, compounds of formula I may also generate antimicrobial compounds. Suitable examples of these compounds are found in, e.g., J. J. Kabara, Cosmet. Sci. Technol. Ser. (16) 1997, p 181–208, especially in Table 8.6, which reference is also incorporated by reference as if recited in full herein.

Of course, the aforementioned oximes, ketones, aldehydes, lactones, alcohols, phenols, amines, and nitriles may serve multiple functions as, e.g., fragrances, flavors, masking agents and antimicrobial compounds, respectively. A person of skill in the art is well aware of these interrelationships and may make use thereof to solve a specific problem by using the precursors of the present invention.

It is not possible to provide a complete list of the organoleptic odor masking, and/or antimicrobial oximes, ketones, aldehydes, lactones, alcohols, phenols, polymeric alcohols, amines, and nitriles which are generated as a result of the desired cleavage of the compounds of formula I by, e.g., skin bacteria, enzymes, elevated temperatures or acidic and/or alkaline pH-values. All such compounds are within the scope of the present invention so long as they may be generated using a precursor compound according to the present invention.

In another embodiment, the compounds of formula I are used as sustained release odorants to mask or attenuate undesirable odors or to provide additional odors not initially present in a consumer product, for example, a personal care product such as a cosmetic product that is applied to human skin. Examples of such cosmetic products include underarm deodorants, antiperspirants, or other deodorants contacting the body; hand lotions; hair care products such as shampoos and conditioners; baby powders; baby lotions; ointments; foot products, facial cleansers; body wipes; facial makeup; colognes; after-shave lotions; shaving creams; and the like.

Additional products into which compounds of formula I may be added include laundry detergents, fabric softeners, fabric softener sheets, (automatic) dishwasher detergents, and all-purpose and hard surface cleaners. Further products into which compounds of formula I may be added include air fresheners and odorants, candles, odor masking agents, and/or antimicrobial agents.

In the present invention, the amount of a compound of formula I required to produce the desired, overall effect varies depending upon the particular compound selected, the product in which it will be used, and the particular effect desired.

For example, when a compound of formula I is added either singly or as a mixture, e.g. to a deodorant or laundry product composition at levels ranging from about 0.1% to about 10% by weight, preferably from about 0.25% to about 4% by weight, an odorant, i.e. one or more odoriferous compounds in an "organoleptically effective amount" is released when the product is used. This newly formed odorant enhances the odor of the product itself or of a fragrance present in the product.

As is evident from the above compilation of oximes, ketones, aldehydes, lactones, alcohols, phenols, and amines a broad range of known odorants may be generated from precursors of the invention. In the manufacture of e.g., consumer product compositions, the precursors of the invention may be used according to methods known to the perfumer, e.g. by W. A. Poucher, Perfumes, Cosmetics, Soaps, 2, 7th Edition, Chapman and Hall, London, 1974.

Compounds of the formula I may be synthesized in a variety of ways known to those skilled in the art. Convenient methods are outlined in the examples set forth below without limiting the invention thereto. For example, the esters may be synthesized via a lipase catalyzed reaction of oximes and vinyl esters (see, e.g., Synthesis, p. 73, 1993) or as exemplified hereafter. The carbonates may be synthesized from the oxime, phosgene, and the alcohol (see, e.g., Tetrahedron Letters, 49, p. 4393, 1975) or also as exemplified hereafter.

The following examples are provided to further illustrate the synthesis of the precursors of the present invention, as well as certain physical properties thereof. These examples are illustrative only and are not intended to limit the scope of the invention in any way.

EXAMPLES

Example 1

(a) Synthesis of octanoic acid 1-bicyclo-[2.2.1]hept-5-en-2-yl-ethanone oxime ester To a suspension of 16.2 g sodium caprylate in 200 ml of acetone, 10.5 ml ethyl-chloroformate was added. The mixture was cooled to −5° C. and 1 ml of pyridine was added. After 40 minutes at −5° C., a solution of 15.12 g of 1-bicyclo[2.2.1]hept-5-en-2-yl-ethanone oxime in 100 ml of acetone was added. After stirring for 5.5 hours at room temperature, the mixture was filtered through Celite and the filtrate was evaporated to dryness. The residue was diluted with ethyl acetate and washed with water, saturated sodium bicarbonate, and water again. The organic phase was dried, filtered, and evaporated to dryness. The resulting yellow oil was purified by chromatography to yield 18.6 g of a colorless oil.

NMR (CDCl$_3$) δ 6.30–6.08 (m, 1H), 5.98–5.77 (m, 1H), 3.23–3.08 (m, 1H), 3.07–2.93 (m, 1H), 2.93–2.80 (m, 1H), 2.50–2.31 (t, 2H), 1.89 (s, 3H), 1.79–1.57 (m, 2H), 1.56–1.41 (m, 2H), 1.41–1.12 (m, 10H), 1.03–0.78 (m, 3H).

(b) Synthesis of octanoic acid 5-methyl-heptan-3-one oxime ester

Using the same procedure in Example 1(a), octanoic acid 5-methyl-heptan-3-one oxime ester was prepared from 5-methyl-heptan-3-one oxime, sodium caprylate, ethyl-chloroformate, and pyridine.

(c) Synthesis of benzoic acid 5-methyl-heptan-3-one oxime ester

Using the same procedure in Example 1(a), benzoic acid 5-methyl-heptan-3-one oxime ester was prepared from 5-methyl-heptan-3-one oxime, sodium benzoate, ethyl-chloroformate, and pyridine.

Example 2

Synthesis of 4-oxo-decanoic acid 5-methyl-heptan-3-one oxime ester

A solution containing 24.75 g 4-oxo-decanoic acid, 19.07 g 5-methyl-heptan-3-one oxime, 28.56 g N,N'-dicyclohexyl-carbodiimide, and 1.68 g 4-pyrrolidinopyridine in 400 ml of dichloromethane was stirred for 24 hours at room temperature. The precipitate was filtered off, the filtrate was diluted with ether, washed with aqueous hydrochloric acid, saturated NaHCO$_3$, and brine. The organic phase was dried, filtered, and evaporated to dryness. The resulting oil-crystal mixture was purified by chromatography to yield 28.75 g of a colorless oil.

NMR (CDCl$_3$) δ 2.91–2.62 (m, 4H), 2.56–2.01 (m, 6H), 1.85–1.04 (m, 14H),1.03–0.75 (m, 9H) ppm.

Example 3

(a) Synthesis of methyl-heptan-3-one O-(4-allyl-2-methoxy-phenoxycarbonyl) oxime A solution containing 7.47 g 5-methyl-heptan-3-one oxime and 6.33 g pyridine in 120 ml of dichloromethane was cooled to 5° C. Then, a solution of 13.00 g eugenol-chloroformate in 30 ml of dichloromethane was added to the solution and the resulting mixture was stirred for 68 hours at room temperature. Then, the mixture was acidified with aqueous hydrochloric acid, extracted with ether, washed with aqueous hydrochloric acid, saturated NaHCO$_3$, and brine. The organic phase was dried, filtered, and evaporated to dryness. The resulting oil was purified by distillation and chromatography to yield 13.26 g of a colorless oil.

NMR (CDCl$_3$) δ 7.25–7.02 (m, 1H), 6.92–6.71 (m, 2H), 6.10–5.83 (m, 1H), 5.30–5.01 (m, 2H), 3.81 (s, 3H), 3.54–3.29 (d, 2H), 2.65–2.27 (m, 4H), 1.90–1.07 (m, 6H), 1.06–0.71 (m, 6H) ppm.

(b) Synthesis of 5-methyl-heptan-3-one O-(3-methyl-5-phenyl-oxycarbonyl) oxime

Using the same procedure in Example 3(a), 5-methyl-heptan-3-one O-(3-methyl-5-phenyl-oxycarbonyl) oxime was prepared from 5-methyl-heptan-3-one oxime and 3-methyl-5-phenyl-pentanol chloroformate.

Example 4

Detergent-Containing Precursor Compounds

Test cloth was washed with a lipase-containing detergent to which the precursor of Example 1(a) had been added. Headspace analysis of the wet and dry laundry indicated the presence of the decomposition product 1-bicyclo [2.2.1] hept-5-en-2-yl-ethanone oxime, which is a fragrance with the common name Terravert. The fragrance level was higher compared to the test cloth washed with a lipase-containing detergent to which an equivalent amount of Terravert had been added.

Analogous experiments were performed with the other precursor compounds synthesized in Examples 1–3. In each of these experiments, the result was the same. The fragrance level in the wet and dry laundry was always higher when washed with a detergent containing a precursor of the present invention compared to laundry washed with a detergent containing an equivalent amount of the appropriate fragrance.

Example 5

Fabric Softener-Containing Precursor Compounds

Test cloth was washed with a lipase-containing detergent and then a fabric softener containing one or more of the precursors of Examples 1–3 that was/were added to the rinse cycle. Headspace analysis of the wet and dry laundry indicated the presence of the appropriate odoriferous decomposition products, i.e. the fragrances. The fragrance level was higher in the test cloth washed and treated with a frabric softener containing a precursor compound of the present invention compared to test cloth washed and treated with a fabric softener containing an equivalent amount of the corresponding fragrance(s).

Example 6

Activation with Axilla Cultures

Axilla bacteria cultures, each containing 0.1% of a precursor compound of Examples 1–3 were prepared, and then incubated for 20 hours at 30° C., whereby the precursors were decomposed and formed, inter alia, fragrant decomposition products, i.e., fragrances (oxime, and alcohol in the cases of Examples 3a and 3b). After filtration from the cells, the presence of the corresponding fragrance was in each case detected by headspace-GC techniques and/or the majority of an 18 member panel.

The same tests were carried out with inactivated cultures and, further, extended to 85° C. for 20 minutes. The odor of the corresponding fragrance after incubation was not detectable in any of these cases, therefore excluding a hydrolysis by the medium or the culture.

Example 7
Use of Precursors in Commercial Compositions

The following examples illustrate the use of the compounds of the present invention in various consumer products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones, and the like. All products may also be buffered to the desired pH. All values are % w/w. In the following examples, the phrase "Delayed Release Fragrances" refers to any one of the compounds set forth in Examples 1–3.

a) Deo-colognes

|  | A | B | C | D |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciby Geigy) | 1.0 | — | 0.75 | 1.0 |
| Alcohol to | 100 | 100 | 100 | 100 | b) Deo-Sticks

| | % |
|---|---|
| Antiperspirant: | |
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminum Sesquichlorhydrate | 20.0 |
| Delayed Release Fragrances | 0.5 |
| Fragrance | 0.5 |
| Steary Alcohol | 17.0 |
| Castor Wax | 3.0 |
| Talc | 5.0 |
| Aluminum Zirconium Tetrachlorhydrate | 20.0 |
| Delayed Release Fragrances | 1.0 |
| Fragrance | 1.0 |
| Dimethicone Dow 245 | to 100.0 |
| Clear Deodorant Stick: | |
| Witconol APM | 43.0 |
| Propylene Glycol | 20.0 |
| Alcohol 39C | 20.0 |
| Demin Water | 7.0 |
| Monamid 150ADD | 5.0 |
| Millithix 925 | 2.0 |
| Ottasept Extra | 0.5 |
| Delayed Release Fragrances | 0.75 |
| Fragrance | 0.75 |
| Deodorant Stick: | |
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |
| Alcohol free Deodorant Stick: | |
| PPG-3 Myristyl Ether (Witconol APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |
| Antiperspirant Aerosol: | |
| Absolute Ethanol | 15.0 |
| Zirconium Aluminum Tetrachlorhydrate | 5.0 |
| Bentone 38 | 1.5 |
| Delayed Release Fragrances | 0.75 |
| Fragrance | 0.75 |
| S-31 Hydrocarbon propellant | to 100.0 |
| Antiperspirant Pump: | |
| Demin Water | 57.5 |
| Aluminum Sesquichlorhydrate | 20.0 |
| Triton X-102 (Union Carbide) | 2.0 |
| Dimethyl Isosorbide (ICI) | 20.0 |
| Delayed Release Fragrances | 0.25 |
| Fragrance | 0.25 |
| Roll-On: | |
| Dimethicone DC 354 (Dow Corning) | 69.0 |
| Bentone 38 | 10.0 |
| Rezal 36 GP (Reheis Chem. Co.) | 20.0 |
| Delayed Release Fragrances | 0.5 |
| Fragrance | 0.5 |

In the above examples the following components were used:

| | |
|---|---|
| Triclosan | 5-chloro-2-(2,4-dichlorophenoxy) phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150 ADD | cocoamide diethanolamine |
| Millithix 925 | dibenzylidene sorbitol |
| Ottasept Extra | quatemium 18 hectorite |
| Bentone 38 | quatemium 18 hectorite |
| Triton X-102 | octoxynol-13 |
| Dimethicone DC 354 | mixture of fully methylated linear siloxane polymers end-blocked with trimethylsiloxy units |
| Rezal 36 GP | Aluminum zirconium tetrachlorohydrexglycine |

When applied to human skin, all of the malodor preventing products set forth above containing the "Delayed Release Fragrances" upon decomposition showed more intense and longer lasting effects compared to equivalent products containing the same amount of the corresponding fragrance.

Example 8
Precursors in Fabric Softeners

The following two examples exemplify the production of fabric softeners containing at least one of the precursors of Examples 1–3 that form delayed release fragrances as decomposition products. These softeners have the advantages as already explained in Example 5.

a) Fabric softener of the ester quat type (4× concentrate):

| ingredients | chemical name | % |
|---|---|---|
| PHASE A | | |
| deionised water | | to 100.0 |
| MgCl$_2$ (saturated sol.) | Magnesium chloride | 1.0 |
| PHASE B | | |
| Rewoquat WE 18 | Di-(tallowcarboxyethyl)hydroxy ethyl methylammonium methosulfate | 15.0 |
| Genapol O 100 | Ethoxylated fatty alcohol C16–C18 10EO | 2.0 |
| antifoam DB 31 | | 0.5 |

| ingredients | chemical name | % |
|---|---|---|
| PHASE C | | |
| isopropyl alcohol | | 3.0 |
| preservative | | Qs |
| precursor and perfume | | Qs |

Preparation Process:

While stirring and heating to 65° C., part A was admixed, then part B was preheated to 65° C. and then added to part A. After cooling to room temperature, part C was added to the mixture of A and B.

The pH value of the finished product was 2.60. The recommended level of the precursor and perfume is 1.0%. Delayed release fragrances of Examples 1–3 may be any part of this 1.0%.

b) Fabric softener of the ester quat type (1× concentrate):

| ingredients | chemical name | % |
|---|---|---|
| PHASE A | | |
| deionised water | | to 100.0 |
| PHASE B | | |
| Rewoquat WE 18 | Di-(tallowcarboxyethyl)hydroxy ethyl methylammoniummethosulfate | 6.0 |
| Dobanol 25-9 | Ethoxylated fatty alcohol C12–C15 9EO | 0.50 |
| antifoam DB 31 | | 0.10 |
| PHASE C | | |
| Myacide BT 30 | 2-bromo-2-nitropropane 1,3 diol | 0.03 |
| Proxel GXL | Benzisothiazolinone sodium salt | 0.02 |
| precursor and perfume | | Qs |

Preparation Process:

While stirring and heating to 65° C., part A was admixed, then part B which had been preheated to 65° C. was added to part A. After cooling to room temperature, part C was added to the mixture of A and B.

The pH value of the finished product was 3.5. The recommended level of the precursor and perfume is 0.3%. The "Delayed Release Fragrances" of Examples 1–3 may be any part of this 0.3%.

The invention being thus described, it will be obvious that the same may be varied in many ways. Such variations are not to be regarded as a departure from the spirit and scope of the invention and, all such modifications are intended to be included within the scope of the following claims.

We claim:

1. 2,6-diemethyl-oct-5-enal.

* * * * *